United States Patent [19]

Persson et al.

[11] Patent Number: 4,970,085
[45] Date of Patent: Nov. 13, 1990

[54] PROCESS FOR MAKING IMPROVED CITRUS AQUEOUS ESSENCE AND PRODUCT PRODUCED THEREFROM

[75] Inventors: Louis T. Persson, San Diego, Calif.; Lester P. Van Brocklin; Lowen R. Morrison, Jr., both of Cincinnati, Ohio; Claudia A. Smith, Loveland; Donald R. Meece, Cincinnati, both of Ohio

[73] Assignee: The Procter & Gamble Company, Cincinnati, Ohio

[21] Appl. No.: 423,921

[22] Filed: Oct. 19, 1989

[51] Int. Cl.[5] .............................................. A23L 2/06
[52] U.S. Cl. ................................. 426/330.5; 426/590
[58] Field of Search .................. 426/330.3, 599, 330.5, 426/490, 422, 478

[56] References Cited

U.S. PATENT DOCUMENTS

| | | |
|---|---|---|
| 2,773,774 | 12/1956 | McCarthy et al. |
| 3,071,474 | 1/1963 | Gross |
| 3,418,134 | 12/1968 | Rooker |
| 3,477,856 | 11/1969 | Schultz |
| 3,782,972 | 1/1974 | Atkins et al. |
| 3,917,865 | 11/1975 | Shaw et al. |
| 3,989,854 | 11/1976 | Chandler et al. |
| 4,374,865 | 2/1983 | Strobel |
| 4,435,437 | 3/1984 | Ziegler |
| 4,647,466 | 3/1987 | Japikse et al. |

FOREIGN PATENT DOCUMENTS 0110638 6/1984 European Pat. Off.

OTHER PUBLICATIONS

Moshonas 1986 Food Technology Nov. 1986 pp. 100-103.
Snyder & Kirkland, Introduction to Modern Liquid Chromatography, Second Edition, John Wiley & Sons, Inc., New York, pp. 15-81 (1979).
Ehntholt et al., Isolation and Concentration of Organic Substances from Water, U.S. Dept. of Commerce, Springfield, Va., (Abstract) (1984).
Hassler, Purification with Activated Carbon, Chemical Publishing Co., Inc., New York, N.Y., pp. 50, 106, 282-283, and 319-321 (1974).
Helfferich and Klein, Multicomponent Chromatography, Theory of Interference, Marcel Dekker, New York, pp. 170-173 (1970).
Frenz and Horvath, High Performance Displacement Chromatography: Calculation and Experimental Verification of Zone Development, AICHE J., 31, p. 400 (1985).
Shaw, "The Flavor of Nonalcoholic Fruit Beverages", U.S. Citrus & Subtropical Products Laboratory, Elsevier Scientific Publishing Co. (1985).
Mattson et al., Activated Carbon: Surface Chemistry and Adsorption from Solution, Marcel Dekker Inc., New York, pp. 205-207 (1971).

Primary Examiner—Carolyn Paden
Attorney, Agent, or Firm—Gary M. Sutter; Ronald L. Hemingway; Richard C. Witte

[57] ABSTRACT

The invention is a method for making improved citrus aqueous essences by a fractionation process wherein citrus aqueous essence is first passed through a solid adsorbent so that part of the essence compounds exit the adsorbent in a first effluent and part remain on the adsorbent, and then at least part of the first effluent is recycled through the adsorbent to recover a fraction of the remaining compounds and produce a second effluent.

14 Claims, 3 Drawing Sheets

PROCESS FOR MAKING IMPROVED CITRUS AQUEOUS ESSENCE AND PRODUCT PRODUCED THEREFROM

TECHNICAL FIELD

The present invention relates to the area of aqueous essences derived from citrus fruits such as oranges. More particularly, the invention relates to a process for making improved aqueous essences and essence fractions for blending, by passing the essences through a solid adsorbent such as activated carbon.

BACKGROUND OF THE INVENTION

Freshly extracted citrus juice is subjected to a concentration step to store and preserve the juice for year-round consumption. Evaporation removes water from the fresh juice, and organic flavor and aroma compounds are removed with the vapor stream. The vapor stream condenses into a concentrated two-phase system. The water phase is referred to as "aqueous essence" and the oil phase is referred to as "essence oil".

Aqueous essence consists primarily of water, along with amounts of organic compounds such as low molecular weight alcohols (e.g., ethanol), aldehydes and esters. The essence is often added back to the concentrated juice to improve its flavor. However, aqueous essence obtained in the above-described method contains some organic compounds, especially components from peel oil, which impart off-flavors to the juice as well as those which impart good flavors. These off-flavors in the aqueous essence as produced by the concentration step then limit the amount of essence which can be added back to juice, in turn limiting concentrations of the good flavors from the essence which can be formulated in the final juice. Therefore, there is a need for improved aqueous essences containing high concentrations of good flavor compounds and fewer off-flavor compounds.

Several references disclose the use of activated carbon to enhance the flavors of fruit juices. For example, U.S. Pat. No. 3,071,474, issued to Gross (1963) discloses a process for the recovery of volatile flavoring compounds normally lost during fruit juice processing. The volatile flavors are trapped by adsorbing them on a suitable adsorbent such as activated charcoal. For example, the charcoal can be placed in the vapor line of a vacuum evaporator used to concentrate fruit juices. The charcoal picks up the volatile flavors while permitting the water vapor to pass on through to be condensed in the usual manner. Compounds of lower boiling points and lower molecular weight can be released from the activated charcoal by the use of a solvent such as an ether or hydrocarbon, and the flavors can then be added back to the juice. Example IV of the patent discloses an orange juice made according to the process.

U.S. Pat. No. 3,418,134, issued to Rooker (1968) discloses a process for adsorbing released volatile aromatics on activated charcoal prior to their deterioration in the preparation of concentrates from coffee, tea or cocoa. The process can also be used to adsorb volatile-containing aromatics released during conventional processing of a natural fruit product, such as the production of a fruit concentrate. The adsorbed aromatics are extracted from the charcoal by a solvent such as one of the chlorofluoromethanes and then added back to the juice.

U.S. Pat. No. 2,773,774, issued to McCarthy et al. (1956) discloses a process in which fruit juice is concentrated by evaporation of water therefrom at low temperatures under vacuum, and volatile flavoring materials are recovered from the vaporized water and returned to the concentrated juice. The process is particularly suited for citrus juices such as orange juice. The flavoring materials vaporized with the water in the concentration process are substantially all separated from the water by adsorption on a solid adsorbent such as activated carbon, particularly activated charcoal. The flavoring materials are steam stripped from the charcoal and returned to the juice.

Hassler, *Purification with Activated Carbon*, Chemical Publishing Co., Inc., New York, NY, pages 50, 106, 282-283, and 319-321 (1974), discloses that activated carbon can be used to decolorize fruit juices such as cherry juice, and to remove unpleasant taste caused by fermentation or other contamination from fruit juices such as pineapple juice.

In the Gross, Rooker and McCarthy et al. processes the solid adsorbent is used to adsorb volatile compounds from a vapor, not from a liquid as in the present invention. The volatile compounds of the prior art processes are the very high volatiles that are lost during evaporation, not compounds such as ethyl butyrate and hexanal. The Gross, Rooker and McCarthy et al. processes would not produce good fractionation of aqueous essence organic compounds.

Further, the use of solvents as in the Gross and Rooker patents has drawbacks because the solvents must be introduced from outside the process, resulting in added expense and the loss of an "all natural" product. The solvents are generally not food approved, and it is very difficult to remove all the excess solvent, usually by an added distillation step. None of the references suggests using citrus essence itself as the solvent, as in the present invention.

Aqueous essence is generally fractionated industrially by thermal distillation. This method can remove many off-notes, especially heavier compounds such as linalool. However, some off notes are difficult to remove by distillation. For example, ethyl butyrate and hexanal are difficult to separate because their boiling points are very similar. Hexanal removal is of particular importance, due to its negative flavor impact at higher concentrations.

Good analytical scale fractionation of chemical compounds can sometimes be obtained by using various forms of chromatography. Elution chromatography is a method commonly used for such analytical separations. In Snyder and Kirkland, *Introduction to Modern Liquid Chromatography*, 2nd Ed., John Wiley & Sons, Inc., NY, p. 15 (1979) descriptions are given of various forms of the method. The method employs two steps: first, the organic mixture of interest, dissolved in an external solvent, is loaded (adsorbed) onto the front end of a chromatographic bed (column). Second, another external solvent is moved through the column. The physical properties of the bed are chosen such that the compounds, while dissolved in the second solvent, have different affinities one from another for the bed. Also, the second solvent is chosen for the capability to dislodge the compounds from the bed. In this way the flowing solvent causes compounds to move down the bed at different rates. With a sufficiently long bed, compounds of different affinities can be completely separated one from the other in chromatographic "peaks". By collecting individual column effluent fractions containing only the "peaks" of interest, individual compounds can be separated.

While elution chromatography is effective for analytical chemistry and is a well developed technology, especially for small scale separations, the approach has disadvantages for larger scale operations needed to produce quantities of various materials for industrial use. First, an isocratic elution process (constant composition solvent) always dilutes the compounds with an unwanted solvent, frequently to levels much lower than the concentration of the compounds in the first loading step This is inherent in the isocratic elution process, because a significant amount of solvent is used to move compounds down the bed and away from one another. Gradient elution (solvent composition is gradually changed) can be used to maintain or increase concentrations, but this introduces additional unwanted solvent and is generally not appropriate for the type of operations described in this patent.

As a consequence, individual flavors produced by isocratic elution chromatography usually are heavily diluted and are not useful as produced. The dilute flavors obtained from elution usually must be thermally concentrated before use. The second disadvantage is the frequent requirement to completely remove the external elution solvent to produce an acceptable product.

An approach more amenable to large scale operation is frontal chromatographic separation. In Helfferich and Klein, *Multicomponent Chromatography, Theory of Interference*, Marcel Dekker, NY, p. 170-173 (1970) the method is described. In this method the adsorbent bed is first presaturated with solvent. Then, the flow is begun to the column of the organic mixture to be separated and the effluent from the bed is captured in fractions. As the mixture proceeds down the bed the component with the lowest affinity for the bed moves fastest down the bed and exits first. This first wave is a pure component. Following the first wave is a second corresponding to the component with the second lowest affinity for the fixed bed. This second wave also contains some of the first component. Similarly, the third wave contains the component with the third lowest affinity, as well as some of the first two components. This process can be continued until all components have broken through. At this point the liquid exiting the bed has the same composition as the column feed.

At breakthrough of the first component, i.e., the lowest affinity component, its concentration in the effluent is at least equal to, but often greater than its original concentration in the feed. The same is true for all components as they breakthrough in the effluent. Fractions are carefully collected and the process is continued until all components have individually broken through. In practice we seldom collect all fractions, because to obtain a useful separation the flow is stopped just as an undesirable component begins to break through into the effluent. At this point a significant portion of the acceptable, lower affinity components have passed through the bed and are contained in the effluent.

The frontal chromatographic separation method can be summarized as a process for splitting off a group of low affinity compounds from another group of high affinity compounds. Obtaining a pure compound with the solvent is not possible, except for the first breakthrough compound. The significant disadvantage of this method is the relatively poor separation selectivity between individual compounds.

Displacement chromatography, a more selective fractionation method, is sometimes used for larger scale separations. Frenz and Horvath, *High Performance Displacement Chromatography: Calculation and Experimental Verification of Zone Development*, AICHE J., 31, p. 400 (1985), describe this method and discuss how very sharp fronts can be obtained. This method employs two setups. First, the organic mixture of interest, dissolved in a solvent, is loaded onto the front end of the chromatographic column. The procedure is similar to the first part of the elution process, except that a larger portion (for example, one tenth to one half of the column) is loaded with the organic mixture. Second, a displacer with solvent is introduced into the column and permitted to slowly flow through the bed. The primary characteristic of the displacer is that it has a greater affinity for the bed than any of the components to be fractionated. As the displacer flows through the bed all components of lower affinity are pushed ahead of the displacer. With a sufficiently long bed the organic mixture resolves into a series of pure components in a sequence corresponding to the affinity sequence of the compounds. (Except, compounds with equal affinities will not separate one from the other.) The first component to emerge will be the species with the lowest affinity and will be a pure component in solvent. Immediately following will be the next lowest affinity component, also as a pure component in solvent. The third lowest affinity component emerges and so on until the displacer emerges. All components will be pure components in solvent, except for the crossover between adjacent compounds caused by axial dispersion or mass transfer resistance. Usually the bed is initially loaded with sufficient material that individual pure compounds can be obtained if desired.

The advantage of this process is that pure components can be obtained or individual negative flavors removed at will. Another advantage is the maintenance or sometimes increase in the concentration of components relative to the feed composition. This obviates the need for an expensive and complex concentration step after the fractionation.

The primary disadvantage of displacement chromatography is the difficulty in finding a suitable displacer. An ethanol/water system is a satisfactory eluent for an orange essence system, but it does not displace the flavors of primary interest. In a food system a natural material, preferably from the system itself, is most desirable. Unless the displacer is low cost, it must be recovered and recycled, usually an expensive route.

None of these references or the methods known to the art provide a simple, cost-efficient process with high recovery of valuable flavors while finely fractionating aqueous essences, and without thermal degradation. (These are requirements for a commercial process.) In particular, none provides a method for making improved citrus essences that have a high concentration of the good flavor compounds ethyl butyrate, ethyl acetate, and acetaldehyde, while containing low amounts of off-flavor compounds such as hexanal, linalool, and alpha-terpineol.

Therefore, it is an objective of the present invention to provide a process for making improved citrus aqueous essences that are high in good flavor compounds and low in off-flavor compounds, while maintaining high recovery of the good flavor compounds. Also, the process does not use external solvents, does not use a displacer, and does not use thermal distillation.

It is another object of the present invention to make the improved aqueous essences by a process involving passage of aqueous essence blends through a solid adsorbent such as activated carbon.

These and other objects of the present invention will become evident from the disclosure herein.

SUMMARY OF THE INVENTION

The present invention is a process for the production of improved citrus flavor essence compositions. A first preferred embodiment of the invention is a process comprising the steps of: (a) obtaining a citrus aqueous essence containing desired good flavor compounds as well as those which are undesirable; then (b) passing the essence through a solid adsorbent to produce a first effluent, where the passage is stopped at about the breakthrough point of ethyl butyrate; and then (c) recycling the essence through the adsorbent to recover a second effluent, where the recycling is stopped at about the breakthrough point of hexanal.

A second preferred embodiment of the invention is a process comprising the steps of: (a) passing citrus aqueous essence through a solid adsorbent bed in such a manner as to perform frontal chromatographic separation of the essence; (b) collecting fractions of the bed effluent in a sequential manner; (c) stopping flow of the original feed essence at a predetermined composition of the effluent; (d) examining the collected fractions of essence for the presence of undesirable negative flavors; (e) setting aside those fractions containing the undesired negative flavors; (f) recycling the acceptable treated flavor fractions back through the bed in a manner consistent with elution chromatographic fractionation of the flavors remaining on the bed; (g) stopping the elution step when the first pass treated essence is exhausted or when an unacceptable concentration of a negative flavor begins to emerge from the bed. If desired, the set aside essence fractions containing negative flavors from (e) can be passed through a second solid adsorbent bed, performing frontal chromatographic separation of this essence until the negative flavors begin to break through; and (i) compositing treated essences from steps (g) and (h) to produce a final product essence with substantially reduced negative flavors, but with high recoveries of the important light flavor compounds in aqueous citrus essence. The resulting treated essence can be blended with commercially available aqueous essence to enhance the concentrations of acetaldehyde, ethyl acetate, and ethyl butyrate without introducing significant amounts of strong negative flavors such as hexanal or ethyl vinyl ketone which would unbalance or degrade the final juice flavor.

DETAILED DESCRIPTION OF THE INVENTION

Figure 1:
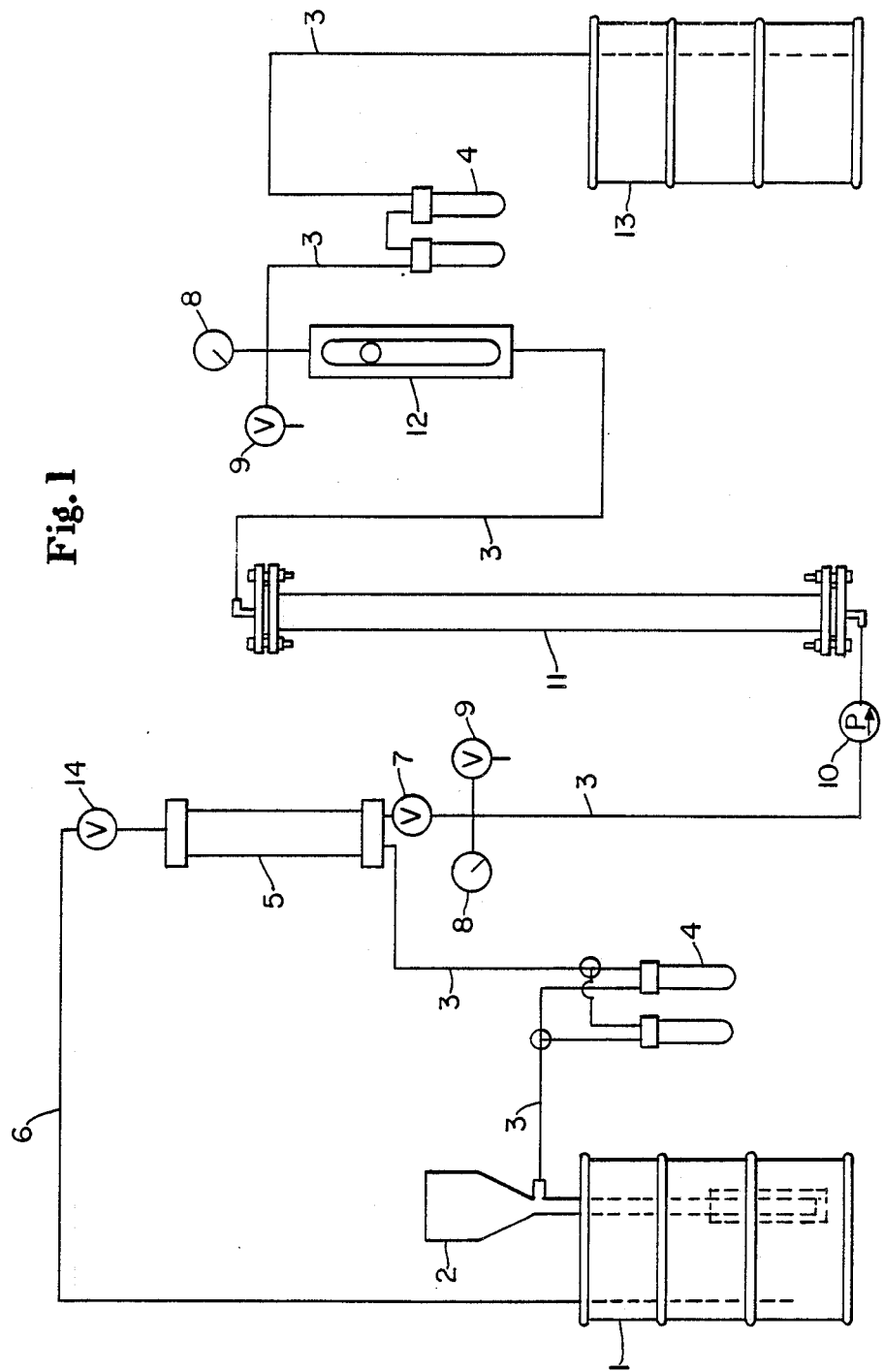
FIG. 1 is a drawing of the chromatographic process and equipment for steps (a), (b), and (c) of the above summary.

The present invention is a process for the fractionation of citrus aqueous essence to provide upgraded natural essences and citrus juice flavor boosters.

Citrus aqueous essence contains a mixture of positive and negative flavor compounds. Known positive flavor compounds in essence include acetaldehyde, ethyl acetate and ethyl butyrate. These compounds give freshness and fruity character to the essence. Negative flavor compounds include hexanal (green off-flavor), linalool (tea off-flavor) and alpha-terpineol (woody off-flavor).

Conventional commercial aqueous essences contain an excess of negative flavor compounds and off-flavors as well as good flavor compounds. If these conventional essences are added as a flavor booster to juice in sufficient quantity to obtain the desired levels of good flavors, significant levels of off-flavors are also added and the flavor balance of the juice is altered. An advantage of the present invention is that it allows the production of a clean essence, that is, an essence that contains a high concentration of the good flavor compounds while containing minimal off-flavors. The essence of the invention can be added to juice in sufficient quantity to obtain a fresh, fruity flavor without ruining the balance of the juice, and without introducing excessive off-notes.

It was surprisingly discovered that an improved aqueous essence according to the present invention can be made by a process in which a commercially available aqueous essence or essence blend which has been passed once through a solid adsorbent to remove the heavy organic compounds, is recycled through the adsorbent to remove certain organic compounds remaining on the adsorbent after the first pass and at the same time maintain both high recovery and approximate feed concentration of important light flavor compounds. The process does not require the use of an external solvent for elution chromatographic fractionation or a displacer for displacement chromatographic fractionation. This results in a simple, low cost process without the requirement for expensive and complex solvent or displacer recovery systems, and it eliminates the problems associated with introducing nonfood or noncitrus sourced materials into the flavor essence and resulting juices.

It was known to the inventors that when citrus aqueous essence is first flowed through an adsorbent, frontal chromatographic fractionation of flavors will take place and compounds will separate in order of some affinity sequence determined by the solvent and adsorbent combination. In general, it was believed that the affinity sequence would be based roughly upon molecular weight, with the heavier compounds tending to remain on the adsorbent and the lighter compounds flowing through the adsorbent first. It was also believed that the frontal chromatographic fractionation would not sharply separate the compounds from each other and, therefore, not give high recovery of the important positive flavor compounds.

Two surprising discoveries have been made. First, it has now been discovered that hexanal follows ethyl butyrate in the chromatographic affinity sequence of aqueous orange essence compounds relative to activated carbon, even though the molecular weight of ethyl butyrate is about one-sixth more than hexanal. This means that frontal chromatography can be used to produce essence free of the undesirable hexanal flavor. However, frontal chromatographic separation alone will not give a good recovery of ethyl butyrate without hexanal. Second, it has now been surprisingly discovered that when the frontal chromatographic step (first pass of essence through the bed) is combined with a second chromatographic step (the recycle of treated essence), the ethyl butyrate and hexanal are much more sharply fractionated in the effluent of the adsorbent bed, compared with the performance of a frontal separation alone.

The second pass chromatographic step with the once treated essence has certain characteristics usually associated with both elution and displacement chromatography. For example, the recycled essence is able to move ethyl butyrate off a carbon bed and obtain good recovery of the compound, indicating that the essence is effective as an eluent for ethyl butyrate. From frontal chromatographic theory it is known that the ethyl butyrate is distributed throughout the bed, so some of that material must move the length of the bed during the recycle step to achieve high recovery. However, the hexanal which is close behind ethyl butyrate in the affinity sequence (Table 3) and close behind ethyl butyrate in the bed (See FIG. 2), does not appear to be moved effectively by the recycle. This is both fortunate and surprising because it is desired to separate these compounds. The significant difference in the ability of the recycled essence to move these two compounds through the bed, and separate them well (an elution characteristic) is clearly unexpected.

Figure 3:
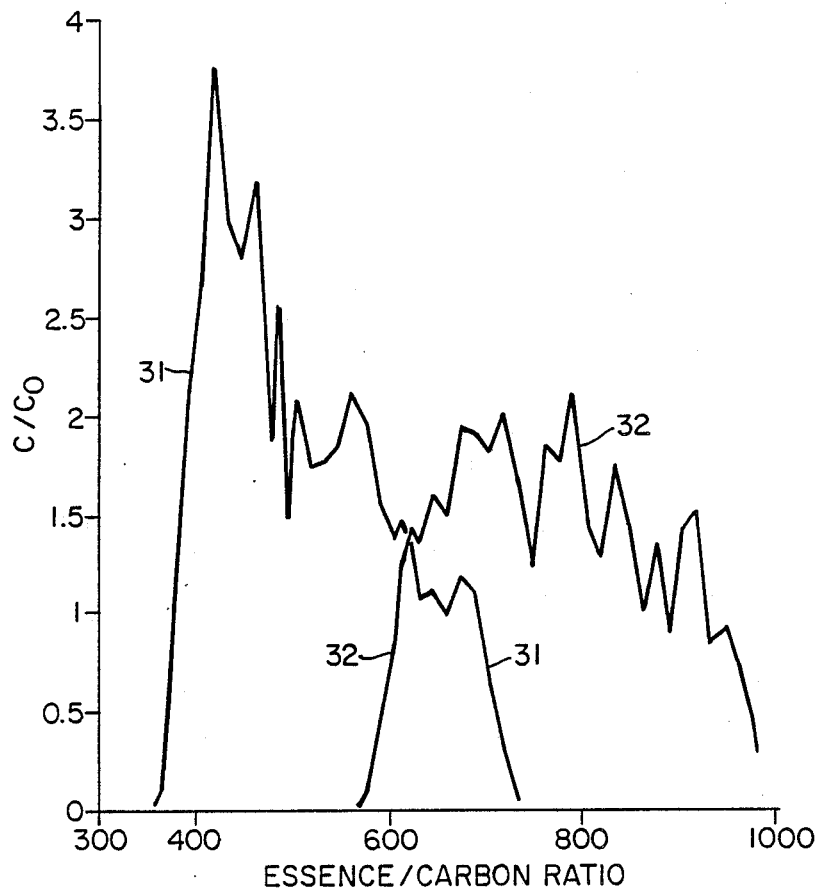
FIG. 3 is a plot showing normalized effluent concentrations of ethyl butyrate and ethyl vinyl ketone versus the ratio of the grams of essence passed through the bed divided by the grams of carbon in the bed for the combined steps (a), (b), (c), (d), (e), (f), and (g) above (second preferred embodiment) for a blended essence consisting of "Natural Redd Aroma" and "Redd Aroma Plus" essences. ("Natural Redd Aroma" and "Redd Aroma Plus" are commercial orange aqueous essences sold by Redd Citrus Specialties, 1711 S. Tenth St., Safety Harbor, FL 34695.) When the essence/carbon weight ratio reaches 621, treated essence minus the ethyl vinyl ketone fractions is recycled through the bed. Also noted on the plot is the essence set aside and not recycled through the bed due to the presence of excessive ethyl vinyl ketone.

The separation characteristics resemble displacement chromatography. This is illustrated by the concentration of the ethyl butyrate which remains about the same or higher than the concentration in the feed essence (See FIG. 3). Additionally, there is not much peak spreading as is typical of elution chromatography. As a result, the separation of ethyl butyrate from hexanal is so good that the desired ethyl butyrate can be nearly completely recovered from the starting essence without the undesired hexanal. It is unexpected that the combination of frontal chromatographic fractionation of blended commercial essence combined with the second step elution chromatographic fractionation using recycled essence would permit such a sharp separation without the application of an external eluent or a displacer.

Table 1 illustrates the difficulty of using only frontal chromatography to separate ethyl butyrate from hexanal. In the Table, recoveries of ethyl butyrate and hexanal are given for selected fractions (which represent the composite of the fraction itself and all previous fractions) while operating in a once through mode. The data correspond both to FIG. 2 and Example 3. The percentages given are weight percents. Fraction 24 indicates a zero recovery of hexanal with only a 50 percent by weight recovery of ethyl butyrate. Higher recoveries of ethyl butyrate are possible, as shown by the subsequent fractions, but the recovery of the hexanal also increases significantly. To avoid hexanal in an improved essence for blending, it is necessary to lose significant ethyl butyrate when only frontal chromatographic separation is practiced. Since citrus sourced ethyl butyrate is very valuable (and sometimes in limited supply), a significant loss of the component is usually unacceptable.

TABLE 1

| Fractions, Composite of All Product Through | Ethyl Butyrate Recovered (wt %) | Hexanal Recovered (wt %) |
|---|---|---|
| 24 | 50.5 | 0.0 |
| 30 | 71.7 | 5.1 |
| 34 | 76.8 | 21.2 |
| 39 | 81.2 | 36.3 |

The advantages of recycling treated essence to achieve a high recovery of ethyl butyrate without hexanal are illustrated by comparing Table 1 to Table 2 which contains data from Example 1. In Example 1 the recovery of ethyl butyrate is 87 percent when zero percent hexanal is recovered. This hexanal recovery corresponds directly to the 50 percent recovery of ethyl butyrate with composite fraction 24, Table 1. Higher recoveries of ethyl butyrate than the 87 percent of Example 1 (a recycle process) are possible by extending the point at which once through flow is stopped and recycle flow started. That is, by accepting a small amount of hexanal, higher recoveries of ethyl butyrate are possible.

TABLE 2

| | Ethyl Butyrate Recovered (wt %) | Hexanal Recovered (wt %) |
|---|---|---|
| Product Using Recycle (Table 6, Example 1) | 87.0% | 0% |

Key to both the sharpness of the separation and the recovery of both ethyl butyrate and hexanal is the point at which the first pass frontal chromatography is stopped and the second pass recycle chromatography is started. By experiment it has been found that stopping the first pass flow at the first appearance of ethyl butyrate will give a satisfactory recovery of ethyl butyrate and no hexanal will enter the effluent In a practical process it may not always be possible or desirable to stop at that point. Further experiments have shown that it is possible to reach a concentration of ethyl butyrate in excess of the feed concentration and still avoid recovering hexanal with the ethyl butyrate during the recycle step. If ethyl butyrate is included in some of the first pass effluent fractions, those fractions containing ethyl butyrate are either used first during the second pass elution or are withheld and used directly in the final product.

In a second embodiment of the present process the ethyl vinyl ketone (EVK), a strong negative flavor, is present in the feed essence at a sufficiently high level (EVK/ethanol ratio at least about 0.00003) to cause unacceptable off notes in the final juice. It has now been surprisingly found that negative flavors on both sides of ethyl butyrate in the affinity sequence can be significantly reduced. In general, this type of separation requires either elution chromatography or displacement chromatography. In the present case it is possible to remove most of the EVK because the affinity of EVK for carbon is less than that of the desired component ethyl butyrate During the first pass frontal chromatographic step the EVK will emerge just before and partially overlap the ethyl butyrate (see FIG. 3). In this case the first pass of essence through the bed is continued into the emergence of ethyl butyrate (about when the essence/carbon weight ratio reaches 600) and then stopped. Those fractions with EVK can then be set aside (and not recycled) along with a small amount of the ethyl butyrate Only EVK free essence need be recycled for the elution step. In this manner most of the EVK can be removed from the essence and the recovery of ethyl butyrate remain high.

The acetaldehyde and ethyl acetate can be recovered from the set aside essence by employing a frontal chromatographic separation. A second carbon bed is fed the set aside essence containing EVK. Flow of essence is stopped when EVK begins to emerge from the bed in the effluent. The EVK free essence from this operation is now composited with the treated essence from the recycle step to produce a final product.

The following Table 3 shows the order in which orange aqueous essence compounds of interest pass through an activated carbon bed (i.e., "affinity sequence"), with methanol passing through first and alpha-terpineol passing through last. This sequence corresponds to the order in which component concentration waves emerge in the effluent during frontal chromatography.

TABLE 3

| Weight Component | Molecular |
|---|---|
| (1) methanol | 32.04 |
| (2) ethanol | 46.07 |
| (3) acetaldehyde | 44.05 |
| (4) butanol | 74.12 |
| (5) diacetyl | 86.09 |
| (6) ethyl acetate | 88.10 |
| (7) 3-methyl-1-butanol | 102.13 |
| (8) methyl butyrate | 100.13 |
| (9) cis-3-hexene-1-ol | 100.16 |
| (10) ethyl vinyl ketone | 84.12 |
| (11) ethyl butyrate | 116.16 |
| (12) t-2-hexenal | 98.15 |
| (13) octanal | 128.22 |
| (14) hexanal | 100.16 |
| (15) linalool | 154.24 |
| (16) alpha-terpineol | 154.24 |

In its broadest aspect, then, the present invention is a process for fractionating citrus aqueous essence, comprising the steps of: (1) passing citrus aqueous essence containing organic compounds through a solid adsorbent so that part of the organic compounds exit the adsorbent in a first effluent, and part of the organic compounds remain on the adsorbent; then (b) recycling at least part of the first effluent through the solid adsorbent to recover a fraction of the remaining organic compounds and produce a second effluent. The second effluent is recovered as the product; it will comprise at least part of the recycled first effluent and a fraction of the organic compounds that remained on the bed after the first pass. A preferred solid adsorbent for use in the invention is activated carbon.

PREFERRED EMBODIMENTS

First Preferred Embodiment

In the first step of the first preferred embodiment of the present invention, a citrus aqueous essence is obtained having an amount and ratio of key essence compounds desired in a treated essence or booster. For example, the essence can be purchased, obtained from a processing unit, or blended from essences from these sources. The essence is passed through a solid adsorbent until some of the ethyl butyrate has passed out of the adsorbent as effluent. The first pass is cut off at ethyl butyrate (a positive flavor) to ensure that the hexanal, linalool and alpha-terpineol (negative flavors) are left remaining on the adsorbent, and the first pass effluent is a clean essence without negative flavors. The first effluent contains mostly ethanol, acetaldehyde and ethyl acetate, along with some ethyl butyrate.

The first effluent is then recycled through the adsorbent, thereby recovering the remaining ethyl butyrate out of the adsorbent while leaving hexanal and the heavier compounds behind on the adsorbent. The product contains ethyl butyrate and the lighter compounds without hexanal and the heavier compounds. For example, using orange aqueous essence enriched in ethyl butyrate as a feed material, hexanal and linalool can be completely eliminated from the essence accompanied by 98% by weight recovery of acetaldehyde and 87% by weight recovery of ethyl butyrate.

Specifically, the first preferred embodiment of the present invention is a process for making an improved citrus aqueous essence comprising the steps of:

(a) obtaining a citrus aqueous essence having an acetaldehyde/ethanol weight ratio of from about 0.005 to about 0.05, an ethyl acetate/ethanol weight ratio of from about 0.0001 to about 0.005, and an ethyl butyrate/ethanol weight ratio of from about 0.0001 to about 0.005; then (b) passing the essence through a solid adsorbent to produce a first effluent, where the passage is stopped at a time between:
  (i) about the time when ethyl acetate reaches its maximum concentration in the effluent; and
  (ii) about the time when the concentration of ethyl butyrate in the effluent again becomes equal to it concentration in the original essence, after the time when the concentration of ethyl butyrate in the effluent reaches its maximum concentration; then (c) recycling at least about 10% by weight of the first effluent through the adsorbent to recover a second effluent, where the recycling is stopped at a time between:
  (i) about the first occurrence of hexanal in the effluent; and
  (ii) about the time when the concentration of hexanal in the effluent again becomes equal to its concentration in the original essence, after the time when the concentration of hexanal in the effluent reaches its maximum concentration.

The preferred point to stop flow of the essence to produce the first effluent is usually just beyond the point at which the concentration of ethyl butyrate in the effluent equals its concentration in the feed.

The flavor compounds acetaldehyde, ethyl acetate and ethyl butyrate enhance the fresh flavor of citrus juice. For an essence containing about 10% ethanol, the starting essence preferably contains at least about 500 ppm by weight acetaldehyde, at least about 10 ppm by weight ethyl acetate, and at least about 10 ppm by weight ethyl butyrate.

The essence is then passed through a solid adsorbent such as activated carbon until the concentration of ethyl butyrate in the effluent equals or somewhat exceeds concentration in the feed. This first effluent is recovered and recycled through the carbon bed. Usually, the last effluent collected is the first to be recycled since this effluent usually contains more desirable flavor compounds, which if recycled first, will appear in the second effluent. At least about 10% by weight of the first effluent is recycled, preferably at least about 40%, more preferably at least about 70%, and most preferably about 100%. The recycling is stopped at about the breakthrough point of hexanal or some time shortly thereafter. Alternatively, the recycling can be stopped when the first effluent is exhausted, which usually occurs at about the hexanal breakthrough point. If the recycle material is exhausted before hexanal breaks through, the process is generally stopped at that point. Stopping the recycling when the first effluent is exhausted can be done in both the first and second preferred embodiments of the present invention.

The resulting effluent is recovered as the product. The product essence contains the ethyl butyrate from the starting essence, along with the ethanol, acetaldehyde and ethyl acetate. Hexanal, linalool, alpha-terpineol and most compounds with six or more carbons remain on the bed and may be discarded. Hence, the resulting essence is relatively high in the desirable good flavor compounds and low in off-flavor compounds. Specifically, an improved citrus aqueous essence prepared according to this process has an acetaldehyde/ethanol weight ratio of from about 0.005 to about 0.05, an ethyl acetate/ethanol weight ratio of from about 0.0001 to about 0.005, an ethyl butyrate/ethanol weight ratio of from about 0.0001 to about 0.005, and an ethyl butyrate/hexanal weight ratio of at least about 5, preferably at least about 10. For an essence containing about 10% by weight ethanol, the product essence contains at least about 500 ppm by weight acetaldehyde, at least about 10 ppm by weight ethyl acetate, and at least about 10 ppm by weight ethyl butyrate The levels of linalool, alpha-terpineol, and compounds with greater than six carbons will be essentially negligible - these compounds will remain on the solid adsorbent.

In a typical process according to the invention, at least about 80% by weight of the acetaldehyde, ethyl acetate and ethyl butyrate present in the starting essence are recovered in the product, while less than about 50% of the hexanal is recovered, preferably less than about 25%.

Second Preferred Embodiment

In a second preferred embodiment of the present invention, an additional step is added to remove ethyl vinyl ketone (EVK) and related compounds from the product essence. It was discovered that when some citrus aqueous essences are processed as described above, the resulting product has a petrochemical off-flavor. While not intending to be bound by theory, it is believed that this off-flavor was exposed by the removal of the peel oil components hexanal, linalool, etc. that had previously been masking the off-flavor. It is also believed that the off-flavor is caused by certain 5-carbon aldehydes and ketones which are degradation and oxidation products derived from the citrus peel. Ethyl vinyl ketone is believed to be both a component of and a marker for these compounds. The level of ethyl vinyl ketone in citrus fruits differs with seasonal and weather variations in growing the citrus fruit, being higher in early/mid fruits and higher in fruits grown during drought years. For citrus aqueous essences having an excess of ethyl vinyl ketone, a second preferred embodiment of the present invention is a process for maintaining the concentration of good flavor compounds, and decreasing the concentrations of both ethyl vinyl ketone and related compounds along with hexanal and related off-flavor compounds In this embodiment, the starting essence is flowed through the activated carbon bed until about the breakthrough point of ethyl butyrate. The first effluent is recovered as a number of fractions. The ethyl vinyl ketone-containing fractions are set aside from the first effluent. Then the first effluent is recycled through the carbon bed. As in the preferred embodiment, the recycling can alternatively be stopped when the first effluent is exhausted. The resulting effluent is recovered as the product. Optionally, the EVK-containing effluent fractions can be passed through a second solid adsorbent to recover acetaldehyde and ethyl acetate.

Specifically, the second preferred embodiment of the present invention is a process for making an improved citrus aqueous essence from an essence having an excess of ethyl vinyl ketone, comprising the steps of:

(a) obtaining a citrus aqueous essence having an acetaldehyde/ethanol weight ratio of from about 0.005 to about 0.05, an ethyl acetate/ethanol weight ratio of from about 0.0001 to about 0.005, an ethyl butyrate/ethanol weight ratio of from about 0.0001 to about 0.005, and an ethyl vinyl ketone/ethanol weight ratio of at least about 0.00003; then (b) passing the essence through a solid adsorbent to produce a first effluent, where the passage is stopped at a time between:
  (i) about the time when ethyl acetate reaches its maximum concentration in the effluent; and
  (ii) about the time when the concentration of ethyl butyrate in the effluent again becomes equal to its concentration in the original essence, after the time when the concentration of ethyl butyrate in the effluent reaches its maximum concentration; then (c) recovering the first effluent and setting aside a portion of the effluent containing ethyl vinyl ketone so that at least about 75% by weight of the ethyl vinyl ketone of the starting essence is removed; then (d) recycling at least about 10% by weight of the remaining first effluent through the adsorbent to recover a second effluent, where the recycling is stopped at a time between:
  (i) about the first occurrence of hexanal in the effluent; and
  (ii) about the time when the concentration of hexanal in the effluent again becomes equal to its concentration in the original essence, after the time when the concentration of hexanal in the effluent reaches its maximum concentration.

Again, for an essence containing about 10% by weight ethanol, the starting essence preferably contains at least about 500 ppm by weight acetaldehyde, at least about 10 ppm by weight ethyl acetate, and at least about 10 ppm by weight ethyl butyrate.

In the step (c) of the above process, the effluent of step (b) is preferably recovered as a number of fractions, and then fractions containing ethyl vinyl ketone are set aside. The undesirable fractions can be identified either by a taster or by analytical means.

The product of this process has an acetaldehyde/ethanol weight ratio of from about 0.005 to about 0.05, an ethyl acetate/ethanol weight ratio of from about 0.0001 to about 0.005, an ethyl butyrate/ethanol weight ratio of from about 0.0001 to about 0.005, an ethyl butyrate/hexanal weight ratio of at least about 5, and an ethyl vinyl ketone/ethanol weight ratio of less than about 0.00002. Preferably, the ethyl vinyl ketone is reduced by at least about 75% by weight compared to the concentration in the starting essence. For an essence containing about 10% by weight ethanol, the product essence preferably contains at least about 500 ppm by weight acetaldehyde, at least about 10 ppm by weight ethyl acetate, and at least about 10 ppm by weight ethyl butyrate.

The first effluent of the first preferred embodiment of the present process can also be recovered as a number of fractions if desired, in the same way that the effluent of the second preferred embodiment is recovered. Recovery as fractions permits the detection and removal of any off-flavors in the essence, not only ethyl vinyl ketone. In both processes, it is not critical whether the fractions are then recycled through the adsorbent in forward, reverse, or random order. Generally, fractions containing ethyl butyrate are recycled through the adsorbent first to maximize the recovery of ethyl butyrate in the product.

Processing Parameters and Definitions

Various types of solid adsorbent are suitable for use in the present invention, for example, activated silica gels, synthetic resin adsorbents, or agglomerates of activated adsorbent earths. However, activated carbon is the preferred adsorbent because of its high loading capacity.

The activated carbon bed used in the process of the invention can be any form of activated carbon or activated charcoal. Activated carbon is generally defined as any form of carbon characterized by high adsorptive capacity for gases and vapors. It typically adsorbs 50% or more of its weight of an organic compound and has little affinity for water vapor.

An example of a preferred activated carbon for use in the invention is Calgon Type ADP Granular Activated Carbon (Calgon Carbon Corporation, P.O. Box 717, Pittsburgh, PA 15230), produced by high temperature steam activation and acid washing. It has the specifications and properties shown in the following Table 4. (This activated carbon is generally sieved once by the inventors to obtain the most preferred 80–150 mesh particle size range disclosed below.)

TABLE 4

| | |
|---|---|
| Iodine Number: | 1200 |
| Ash, Weight %: | 9 |
| Moisture, Weight % (as packed): | 5 |
| Molasses Number: | 350 |
| Screen Size | 80 |
| Smaller than 325 Mesh U.S. Sieve Series, Weight %: | |
| Surface Area m$^2$/g (BET method): | 1525 |

The particle size of the carbon used in the bed will preferably vary between about 20 mesh (U.S. Sieve Series) and about 325 mesh, more preferably between about 80 mesh and about 150 mesh. The length of the carbon bed is at least about 6 inches (15.2 cm), preferably at least about 10 inches (25.4 cm), and more preferably at least about 20 inches (50.8 cm). Longer lengths provide better separation of the essence volatile compounds. The carbon bed can be as long as is practical, but typically the length will be between about 10 inches (25.4 cm) and about 200 inches (508 cm), more typically between about 20 inches (50.8 cm) and about 80 inches (203.2 cm).

Preferably the essence is flowed through the carbon bed at a pressure drop between about 5 psi and about 1000 psi, more preferably between about 5 psi and about 100 psi. By pressure "drop" is meant that the essence is under pressure as it is fed to the carbon bed, and then the essence exits the carbon bed at about atmospheric pressure.

The carbon mesh size, essence pressure drop and essence flow rate are interrelated in a manner well-known to the art. A finer mesh size can be used if higher pressure drop or a slower flow rate is used. Conversely, a coarser mesh size allows the use of a lower pressure drop or a faster flow rate. The essence is preferably flowed through the carbon bed at a rate between about 1 cm/min. and about 10 cm/min., more preferably between about 1 cm/min. and about 6 cm/min.

The process can be conducted at a temperature between about 30° F. (-1° C.) and about 50° F. (10° C.). If the temperature is much below 30° F. (-1° C.) the essence will freeze, and if the temperature is much above 50° F. (10° C.) microbial growth is a problem. Typically the process is run at about 35° F. (2° C.) to 37° F. (3° C.).

The activated carbon is generally discarded after the process steps of the invention are completed. Alternatively, the activated carbon can be recycled by backwashing it with a solvent to remove any flavor compounds remaining on the carbon.

As described hereinabove, the process begins with an essence having a high concentration of acetaldehyde, ethyl acetate and ethyl butyrate. The starting essence is generally obtained by combining natural citrus aqueous essences with commercial aqueous essences that are enriched in the desired good flavor compounds (e.g., ethyl butyrate). However, the invention is not limited by the method of formulating the starting essence. In general, the essence will consist of some combination of natural aqueous essences, enriched aqueous essences, and/or isolated volatile flavor compounds.

The present invention can be used to upgrade the aqueous essences of oranges or any of a variety of other citrus fruits, or mixtures thereof. For example, the citrus fruit can be selected from the group consisting of oranges, grapefruits, lemons, tangerines, limes, kumquats, and mixtures thereof.

In both preferred embodiments of the present process, a first effluent resulting from passing an aqueous essence through the solid adsorbent is recycled through the adsorbent to recover a second effluent. While the "first effluent" to be recycled is generally the effluent produced shortly before in the same process, if desired an equivalent effluent from other process runs can be used for the recycling step. What is critical is that the effluent to be recycled has been processed to remove the majority of the compounds (other than ethyl butyrate) having six or more carbon atoms while leaving in the first effluent some ethyl butyrate and also light compounds having less than 6 carbon atoms. Preferably at least about 90% by weight of the organic compounds (other than ethyl butyrate) having 6 or more carbon atoms are removed.

The present invention has been discussed in terms of good flavor compounds and off-flavor compounds. However, in its broadest embodiment the invention relates to any type of separation of aqueous essence organic compounds from each other, regardless of their flavor contribution.

By "effluent", as used herein, is meant citrus aqueous essence that has passed through the solid adsorbent and come out the other side. By "feed" is meant the aqueous essence starting material that is to be passed through the adsorbent.

By "concentration in the original essence", as used herein, is meant the concentration (ppm by weight) of a citrus aqueous essence organic compound in the original aqueous essence or essence blend that is the starting ("feed") material for the process. This concentration is measured by taking samples through a sample valve installed in front of the carbon bed or other adsorbent.

By "concentration in the effluent", as used herein, is meant the concentration (ppm by weight) of a citrus aqueous essence organic compound in the effluent at the point where the effluent exits the solid adsorbent. This concentration value is not the concentration of the total composited effluent recovered from the process step, but rather it is the concentration of the effluent at that point in time when it is exiting the adsorbent. This concentration is measured by taking samples through a sample valve installed after the exit end of the carbon bed or other adsorbent, or by taking samples as the effluent leaves the process equipment such as through an automatic sampler. The method for measuring the concentration in the original essence and in the effluent is described below in the Analytical Method section.

By "the time when the concentration (of a compound) in the effluent again becomes equal to its concentration in the original essence, after the time when the concentration (of the compound) in the effluent reaches its maximum concentration", as used herein, is defined as follows. As each compound passes through and then out of the adsorbent, its concentration is first very small, then it gradually peaks to reach its maximum concentration, and then it declines. If the operation is a first pass of the essence, the chromatographic behavior is of the frontal type. In that case concentrations decline to the feed concentration. If the operation is a second pass of the essence, the chromatographic behavior is of the elution type. Then the concentration can decline below the initial essence feed concentration.

By "the first occurrence of ethyl butyrate", as used herein, is meant the first time the concentration (ppm by weight) of ethyl butyrate in the effluent exceeds 1% of its concentration in the feed. By "the first occurrence of hexanal", as used herein, is meant the first time the concentration (ppm by weight) of hexanal in the effluent exceeds 1% of its concentration in the feed.

Utility of the Invention

There are many advantages associated with the present process. The process can provide a clean citrus aqueous essence flavor booster not currently available from flavor houses. Furthermore, the booster is "100% pure citrus" and depending on the availability of manufacturing plant essences, may be achieved with little or no additional capital cost. As an added benefit, the value of plant produced essences can be significantly increased.

As explained hereinabove, the effluent recovered from the first pass of essence through the adsorbent is generally recovered as a number of fractions. Importantly, this aspect of the process allows the detection and removal of individual negative flavors such as ethyl vinyl ketone. Undesirable flavors can be detected by a flavorist through sniffing, or by a gas chromatograph. Accordingly, composition adjustments can be made to obtain the optimum desired product. This product optimization cannot be easily done by distillation.

Analytical Method: Quantitative Analysis of Aqueous Essences by Direct Injection Capillary Gas Chromatography This method provides a direct analysis of whole aqueous essences by injection of samples into a split vaporizing injector/capillary gas chromatography system. Processing of the raw data is performed by a data system which automatically calculates mg/ml concentration of calibrated components. An internal standard, cyclohexanone, is used to calculate relative response factors. The percent purity of compounds assayed is used to establish the actual amount of the respective calibrated compounds in order to calculate their detector response factors (See Table 5). This procedure does not need a weight adjustment to compensate for nonvolatile components, or unknowns, since each component is calibrated individually. This methodology is good only for citrus aqueous essences and model mixtures of components contained therein.

A. Instrumental procedure:
Instrumentation

A Hewlett-Packard model HP5890 G.C. with a split/splitless sample injector and a model HP7673 automatic liquid sample injector is used (Hewlett-Packard Co., Palo Alto, CA 94304). The instrument is equipped with a model HP3393 reporting integrator/controller. For analyses the prepared samples are thermostated in the autosampler sample tray at 20° C. (68° F.). The oven is fitted with a polar column (DB WAX, 0.32 mm × 30 m, 0.5 um film thickness, J&W Scientific, Inc., Rancho Cordova, CA 95670). A flame ionization detector is used for detection. For quantitation the analog detector signal is presented to a Nelson Analytical XTRO CHROM II Data System based on a 9000 Series HP300 Desktop Computer (Nelson Analytical, Inc., Cupertino, CA 95014). The data system is used for processing of raw detector data and calculation of the results as part per billion concentrations. Results are reported as mg/ml and can be converted to part per billion (ppb) by using the following calculation (parts per million [ppm] can then be obtained by moving the decimal point):

$$ppb = (mg/ml)/\text{weight of sample (mg/ml)} \times 1 \times E10+6$$

Instrument Conditions Air: 364 ml/min at 38 psi Hydrogen: 21 ml/min at 12 psi Hydrogen (carrier gas): 2.5 ml/min at 20° C. (68° F.) Injector Split Vent Flow: 260 ml/min. Septum Purge Flow: 1–2 ml/min. Nitrogen (detector makeup): 25.6 ml/min. at 40 psi Detector temperature: 350° C. (662° F.) Injector Temperature: 325° C. (617° F.) Injection Volume: 2 ul B. Temperature Profile:

The initial oven temperature is 20° C. (68° F.). The oven is equilibrated at initial temperature for 5 min. before sample injection. After sample injection, the oven is held at initial temperature for 10 min. The oven is then temperature programmed to rise at 1 deg/min to 30° C. (86° F.). The oven temperature is then programmed to 110° C. (230° F.) at 3 deg/min and held for 20 min. The oven post analysis temperature is 200°) C. (392° F.) for 12 min.

C. Analytical Sample Preparation:

Using a Microman positive displacement pipette (Gilson CP250, c/o Raining Inst. Co.), 250 ul of sample is place into a tared amber autosampler vial and the weight recorded (as mg/ml). A four-place analytical balance is used. Add to the sample 250 ul of cyclohexanone internal standard solution (concentration 0.2352 components (See Table 5). The values presented in this table represent those values obtained for the middle level standard calibration solution.

TABLE 5

| | | STANDARD CALIBRATION SOLUTION | | | | |
|---|---|---|---|---|---|---|
| Peak | Compound Name | Ret. Time (min.) | Amount (mg/ml) | Area/Amount | Area | I.S./Compound Area Ratio |
| 1 | Acetaldehyde | 1.67 | 0.0332 | 225632.5 | 7491 | 7.2012 |
| 2 | Ethylacetate | 4.49 | 0.0112 | 195357.1 | 2188 | 24.6545 |
| 3 | Acetal | 4.64 | 0.0100 | 444100.0 | 4441 | 12.1468 |
| 4 | Methanol | 4.96 | 0.0796 | 1198052.8 | 95365 | 0.5657 |
| 5 | Methylpropionate | 5.34 | 0.0114 | 292543.9 | 3335 | 16.1751 |
| 6 | Ethanol | 6.77 | 2.0098 | 269775.6 | 542195 | 0.0995 |
| 7 | Ethylpropionate | 7.55 | 0.0106 | 373396.2 | 3958 | 13.6291 |
| 8 | Diacetyl | 9.10 | 0.0332 | 211746.9 | 7030 | 7.6734 |
| 9 | Methylbutyrate | 9.24 | 0.0111 | 365765.8 | 4060 | 13.2867 |
| 10 | Ethylvinylketone | 11.68 | 0.0100 | 476300.0 | 4763 | 11.3256 |
| 11 | Ethylbutyrate | 13.70 | 0.0214 | 415934.6 | 8901 | 6.0604 |
| 12 | Propanol | 14.87 | 0.0102 | 358431.4 | 3656 | 14.7549 |
| 13 | Ethyl 2-Methylbutyrate | 15.17 | 0.0107 | 460373.8 | 4926 | 10.9509 |
| 14 | Hexanal | 17.76 | 0.0108 | 403888.9 | 4362 | 12.3668 |
| 15 | Butanol | 25.71 | 0.0101 | 408910.9 | 4130 | 13.0615 |
| 16 | Limonene | 27.65 | 0.0106 | 776509.4 | 8231 | 6.5538 |
| 17 | t-2-Hexenal | 29.40 | 0.0105 | 428952.4 | 4504 | 11.9769 |
| 18 | 3-Methyl 1-Butanol | 30.12 | 0.0102 | 441764.7 | 4506 | 11.9716 |
| 19 | Cyclohexanone (I.S.) | 33.36 | 0.2352 | 229353.7 | 53944 | 1.0000 |
| 20 | Octanal | 34.21 | 0.0155 | 273290.3 | 4236 | 12.7347 |
| 21 | Hexanol | 38.37 | 0.0102 | 464803.9 | 4741 | 11.3782 |
| 22 | C-3-Hexen-1-ol | 39.75 | 0.0105 | 449142.8 | 4716 | 11.4385 |
| 23 | t-2-Hexen-1-ol | 40.91 | 0.0105 | 441428.6 | 4635 | 11.6384 |
| 24 | Decanal | 44.79 | 0.0100 | 454400.0 | 4544 | 11.8715 |
| 25 | Linalool | 47.36 | 0.0105 | 508571.4 | 5340 | 10.1019 |
| 26 | Octanol | 47.90 | 0.0104 | 481153.8 | 5004 | 10.7802 |
| 27 | Terpene-ol | 49.81 | 0.0114 | 501754.4 | 5720 | 9.4308 |
| 28 | Nonanol | 54.13 | 0.0104 | 496153.8 | 5160 | 10.4543 |
| 29 | Neral | 54.62 | 0.0073 | 451780.8 | 3298 | 16.3566 |
| 30 | Ethyl 3-Hydroxyhexanoat | 55.15 | 0.0122 | 256475.4 | 3129 | 17.2400 |
| 31 | Alpha Terpineol | 56.56 | 0.0108 | 471388.9 | 5091 | 10.5960 |
| 32 | Valencene | 57.14 | 0.0083 | 551807.2 | 4580 | 11.7782 |
| 33 | d-Carvone | 58.56 | 0.0120 | 475833.3 | 5710 | 9.4473 |
| 34 | Geranial | 59.04 | 0.0107 | 586448.6 | 6275 | 8.5967 |

*These amounts represent the middle level of a three calibration level method. As appropriate, samples falling outside the calibrated method (too concentrated) are diluted and rerun.

mg/ml in water). The resulting sample solution is crimped capped with a Teflon-lined cap and mixed thoroughly before placing in the autosampler tray for analysis.

D. Standard Calibration Procedure:

Calibration standards are prepared in volumetric flasks. A portion of water is added to the flask prior to the addition of standard reference compounds in order to minimize loss of the highly volatiles during preparation of the more aqueous soluble components. A similar procedure was followed for the oil soluble compounds using acetone (purified by fractional distillation) as solvent. Equal amounts of both aqueous and oil soluble fractions were combined to form the calibration standard using acetone as the solvent. The least volatiles are added first followed by the more highly volatile materials. Calibration levels and ranges were chosen based on literature cited aqueous essence values and on experimentally determined values obtained through the use of comparative reference spike solutions. Three standard calibration levels were prepared by dilution with water. Identities were confirmed through the use of coincident elution of references and by gas chromatography/mass spectrometry verification against reference spectra. To perform calibration of the instrument for aqueous essence components the respective standard solutions were prepared for analysis according to the sample preparation procedure. Component retention times, internal standard/compound area ratios and area/amount data were generated by the data system for the purpose of automated quantitation of aqueous essence The following examples are intended only to further illustrate the invention and are not intended to limit the scope of the invention which is defined by the claims.

EXAMPLE 1

This example demonstrates the first preferred embodiment of the present invention.

A carbon bed is prepared in the following manner. A stainless steel tube 101.6 cm long with a 1.00 cm ID is cleaned and packed dry with 41 grams of Calgon type ADP granular activated carbon which has been screened to remove particles smaller in size than 325 mesh and greater than 80 mesh by Tyler sieve sizes. The packed carbon is wetted and rinsed with 200 proof grain ethanol and rinsed again with distilled water. (If the process were to be conducted on an industrial scale, a larger particle size would be used, about 150 mesh, and a lower pressure drop, about 15 psi.)

A process run is then conducted in the following manner. Approximately 23 liters of Redd Aroma Plus (a commercially available orange aqueous essence enriched in ethyl butyrate, sold by Redd Citrus Specialties, 1711 South Tenth St., Safety Harbor, FL 34695) is pumped from a large container through a Beckman Model 110A pump (Beckman Instruments Co., Palo Alto, CA) via a feed line, and then via a feed line through the carbon bed at a rate of about 1 gram/minute. The pressure drop varies between about 650 psi and about 850 psi during the run, and the run is done at a temperature of about 37° F. (3° C.). After going through the carbon bed, the essence flows via a feed line to a Gilson Model FC-100 automatic sampler (Gilson Company, Box 27, 300 W. Beltline, Middleton, WI 53582). The feed line has a pressure gauge and a pressure relief valve.

The effluent is collected from the automatic sampler as a number of discrete fractions of about 1400 grams each. When the concentration (ppm by weight) of ethyl butyrate in the effluent exceeds 1% of the concentration in the feed, indicating that the bulk of the ethyl butyrate is ready to come out of the bed, the loading step is stopped.

The collected effluent fractions are then used as feed to elute the ethyl butyrate. The first collected fraction is passed through the carbon bed in the manner described above, then the second fraction, and so forth, until the original effluent has been passed through the bed a second time. The resulting effluent is a product containing most of the lighter compounds but no hexanal or linalool. Analysts shows that the product contains 87% by weight of the original ethyl butyrate, and it is devoid of hexanal, linalool, d-carvone and all high molecular weight material. About 54% by weight of the trans-2-hexenal is recovered.

Table 6 below illustrates the feed composition, the product composition, and the product yield:

TABLE 6

| Compound | Feed Composition (ppm by wt.) | Product Composition (ppm by wt.) | Product Yield wt. % |
|---|---|---|---|
| Methanol | 5094.3 | 5043.4 | 99 |
| Ethanol | 70000.0 | 70000.0 | 100 |
| Propanol | 35.3 | 29.7 | 84 |
| Acetaldehyde | 882.3 | 864.7 | 98 |
| Acetal | 55.0 | 42.9 | 78 |
| Ethyl Acetate | 95.6 | 94.6 | 99 |
| Diacetyl | 4.1 | 4.1 | 100 |
| Methyl Butyrate | 3.8 | — | — |
| cis-3-Hexen-1-ol | 11.3 | 5.7 | 50 |
| Ethyl Butyrate | 182.2 | 158.5 | 87 |
| trans-2-Hexenal | 59.7 | 32.2 | 54 |
| Octanal | 22.6 | 0 | 0 |
| Hexanal | 69.9 | 0 | 0 |
| Linalool | 16.0 | 0 | 0 |
| a-Terpineol | 7.8 | 0 | 0 |

FIG. 1 shows the equipment used if the process is run on a larger scale. A feed drum 1 contains the Redd Aroma Plus essence. An air driven centrifugal drum pump 2 pumps the essence through a process line 3, through filters 4 and then to a dearater 5. Air bubbles are removed from the essence and returned to the feed drum 1 via air vent line 6. The essence is then fed past a throttle valve 7, a pressure gauge 8 and a sample valve 9, and through a booster pump 10 to the front end of the carbon bed 11. The essence flows through the carbon bed 11 and exits into a process line 3. The essence then flows through a rotometer 12, a pressure gauge 8 and a sample valve 0, then flows through filters 4 and into a product drum 13.

EXAMPLE 2

This example demonstrates the second preferred embodiment of the present invention.

A carbon bed is prepared in the following manner. A stainless steel tube 130 cm long with a 1.09 cm 10 is cleaned and packed dry with 50.8 grams of Calgon type ADP granular activated carbon from which material finer than 150 mesh has been removed by sieving. The carbon bed is rinsed with distilled water to remove fines and partially wet out the carbon.

A blend is made of two distilled orange essences. An analysis of the starting blend (feed composition) is shown below in Table 7. About 31.57 kg. of the blend is pumped from a large container through a Beckman Model 110A pump (Beckman Instruments Co., Palo Alto, CA) via a feed line, and then via a feed line through the packed carbon bed at a rate of 4 grams per minute. The pressure drop is about 43 psi, and the process is done at a temperature of about 37° F. (3° C.). After going through the carbon bed, the essence flows via a feed line to a Gilson Model FC-100 automatic sampler (Gilson Company, Box 27, 300 W. Beltline, Middleton, WI 53582). The feed line has a pressure gauge and a pressure relief valve. Effluent is collected from the automatic sampler as 47 discrete fractions of about 700 grams each. When the concentration (ppm by weight) of ethyl butyrate in the effluent exceeds that in the feed the essence blend is no longer used as feed.

Each fraction is then checked by a taster to determine whether it contains off-odors. Fractions with off-odors are set aside and not used in the elution step. Fractions 27 through 44 are found to contain off-odors, believed to be caused by ethyl vinyl ketone. Fractions 46 and 47 are set aside as final product without being used as recycle because they contain high concentrations of ethyl butyrate.

The remaining fractions are used, in reverse order of their production, to pass through the bed to elute the ethyl butyrate. Fraction 45 is used first, followed by Fraction 26, Fraction 25, and so forth.

The composited product contains a large portion of the original ethyl butyrate and no hexanal or heavier compounds. The amount of ethyl vinyl ketone in the product is greatly reduced. The feed composition, product composition, and product yield are tabulated below in Table 7. Because fractions have been removed, the feed contains 31,574 grams of essence while the product contains 18,620 grams; therefore, the product yield is equal to the product composition divided by the feed composition times (18,620/31,574).

TABLE 7

| | Feed Composition (ppm by wt.) | Product Composition (ppm by wt.) | Product Yield (wt. %) |
|---|---|---|---|
| Acetaldehyde | 1442.0 | 1736.0 | 71% |
| Ethyl Acetate | 70.8 | 67.2 | 56% |
| Ethyl Butyrate | 102.8 | 148.0 | 85% |
| EVK | 6.6 | 2.0 | 18% |
| t-2-Hexenal | 15.9 | 1.9 | 7% |
| Hexanal | 38.3 | 0.0 | 0 |

Preliminary taste data indicates the product essence has an acceptable flavor.

The recovery of the acetaldehyde and ethyl acetate in the composited product above is reduced because a substantial amount of these compounds is contained in the off-odor Fractions 27 through 44 which could not be used as product. To recover the missing acetaldehyde and ethyl acetate, Fractions 27 through 44 are pumped through another carbon bed similar to the one described above, at a rate of about 2.1 grams per minute, and the effluent is collected as seven fractions. Of a total of 11,398 grams effluent from the bed, 7,743 grams are completely free of ethyl vinyl ketone. When the EVK-free fractions are combined with the composited product described above, the recoveries become as shown in the following Table 8:

TABLE 8

|  | wt. % Recovered |
|---|---|
| Acetaldehyde | 90% |
| Ethyl Acetate | 71% |
| Ethyl Butyrate | 85% |
| EVK | 18% |
| t-2-Hexenal | 7% |
| Hexanal | 0 |
| Linalool, d-Carvone | 0 |

EXAMPLE 3

This example demonstrates an experimental process run to examine the composition of successive essence product fractions while operating in a frontal chromatographic mode. The results illustrate how a portion of the ethyl butyrate in essence can be recovered without hexanal and heavier compounds. Further, the results show that high recovery of ethyl butyrate is impossible without recovering some hexanal. That is, there is a tradeoff between recovery of ethyl butyrate and the recovery of hexanal. The results can also be used for future estimation of cutoff points of the first cycle of essence through the adsorbent in the present process.

A carbon bed is prepared in the following manner. A stainless steel tube 25.4 cm long with a 0.995 cm ID is cleaned and packed dry with 10.4 grams of Calgon type ADP granular activated carbon. The packed carbon is wetted and rinsed with 200 proof grain ethanol.

Figure 2:
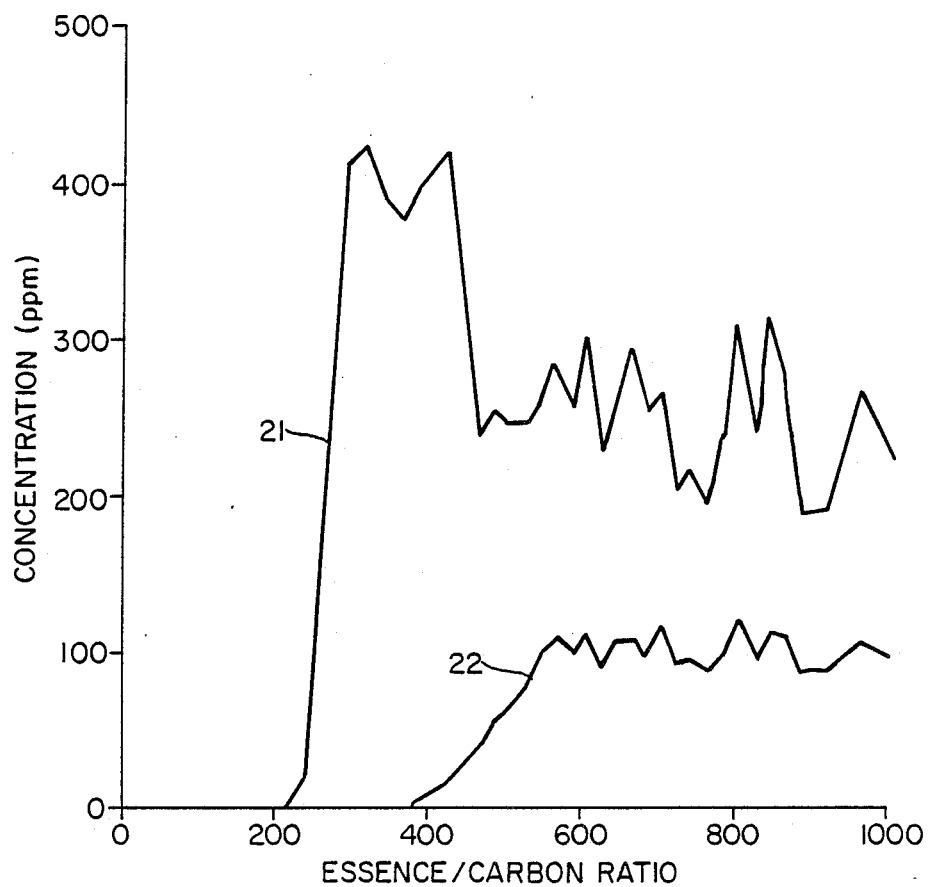
FIG. 2 is a plot showing effluent concentrations of ethyl butyrate and hexanal versus the ratio of the grams of essence passed through the bed divided by the grams of carbon in the bed for frontal chromatographic fractionation of "Redd Aroma Plus" aqueous essence.

A process run is then conducted in the following manner. Approximately 10 liters of Redd Aroma Plus is pumped from a large container through a Beckman Model 110A pump (Beckman Instruments Co., Palo Alto, CA) via a feed line, and then via a feed line through the carbon bed at a rate of about 1 gram/minute. The pressure drop is about 250 psi, and the process is done at a temperature of about 37° F. (3° C.). After going through the carbon bed, the essence flows via a feed line to a Gilson Model FC-100 automatic sampler (Gilson Company, Box 27, 300 W. Beltline, Middleton, WI 53582). The feed line has a pressure gauge and a pressure relief valve. The effluent is collected from the automatic sampler as 57 discrete fractions of about 350 grams each. The fractions are labeled consecutively as Fraction 1 through Fraction 57, with Fraction 1 being the first fraction through the carbon bed. (FIG. 2 presents a composition profile for the discrete fraction compositions versus the essence to carbon weight ratio.)

Table 9 below illustrates several compositions made by combining the fractions, where in this case "Fraction 24" represents the total composition of the combined Fractions 1 through 24, and so forth. In this process run, the essence is pumped through the carbon bed long after the ethyl butyrate and hexanal have broken through. One can use the breakthrough data to decide, for some future run, the cutoff point at which the first cycle should stop. In a frontal chromatographic run with no recycle, the tradeoff is that after the breakthrough of hexanal the recovery of hexanal increases rapidly while the recovery of ethyl butyrate increases slowly. One must decide on an appropriate tradeoff between the recovery of ethyl butyrate and the exclusion of hexanal from ethyl butyrate. One cutoff point, for instance, might be just after the collection of Fraction 30. At this point 71.7% by weight of the ethyl butyrate has been recovered with only 5.1% by weight of the hexanal. Fraction 24 contains no hexanal. In Fractions 44 and 49 the amount of hexanal is too high to be acceptable. In Fraction 57, there is very little hexanal reduction compared to the feed material.

TABLE 9

| | Effluent Fraction (ppm by wt.) | | | | |
|---|---|---|---|---|---|
| Compound | Feed | 24 | 30 | 32 | 34 |
| Acetaldehyde | 773.7 | 772.0 | 778.1 | 771.6 | 776.3 |
| Acetal | 35.9 | 35.4 | 38.2 | 38.3 | 38.8 |
| Methanol | 4568.3 | 4423.0 | 4447.8 | 4444.2 | 4462.5 |
| Propanol | 29.9 | 31.2 | 31.3 | 31.2 | 31.3 |
| Diacetyl | 5.5 | 2.9 | 3.6 | 3.5 | 3.5 |
| Ethyl Acetate | 88.4 | 76.2 | 79.7 | 79.2 | 79.8 |
| Butanol | 4.5 | 0.03 | 0.02 | 1.0 | 1.4 |
| Methyl Butyrate | 3.6 | 3.5 | 3.9 | 3.8 | 3.9 |
| Ethyl Vinyl Ketone | 4.2 | 4.2 | 4.3 | 4.3 | 4.3 |
| Hexanal | 82.0 | 0.0 | 4.2 | 11.0 | 17.4 |
| Ethyl Butyrate | 259.9 | 131.3 | 186.3 | 193.4 | 199.8 |

| | Effluent fraction (ppm wt.) | | | |
|---|---|---|---|---|
| Compound | 39 | 44 | 49 | 57 |
| Acetaldehyde | 770.2 | 765.0 | 771.6 | 751.1 |
| Acetal | 39.0 | 38.7 | 39.0 | 37.5 |
| Methanol | 4460.9 | 4463.5 | 4486.9 | 4417.0 |
| Propanol | 31.2 | 31.0 | 31.2 | 31.0 |
| Diacetyl | 3.4 | 3.3 | 3.3 | 3.2 |
| Ethyl Acetate | 80.0 | 79.3 | 79.1 | 76.7 |
| Butanol | 2.0 | 2.4 | 4.3 | 4.2 |
| Methyl Butyrate | 3.9 | 3.8 | 4.0 | 3.8 |
| Ethyl Vinyl Ketone | 4.3 | 4.3 | 4.3 | 4.2 |
| Hexanal | 29.8 | 38.6 | 46.4 | 51.9 |
| Ethyl Butyrate | 211.1 | 213.6 | 223.2 | 218.6 |

What is claimed is:

1. A process for fractionating citrus aqueous essence comprising the steps of:
   (a) passing citrus aqueous essence containing organic compounds through a solid adsorbent so that part of the organic compounds exit the adsorbent in a first effluent, and part of the organic compounds remain on the adsorbent; then
   (b) recycling at least part of the first effluent through the solid adsorbent to recover a fraction of the remaining organic compounds and produce a second effluent.

2. A process according to claim 1 wherein the solid adsorbent is activated carbon.

3. A process for making an improved citrus aqueous essence comprising the steps of:
   (a) obtaining a citrus aqueous essence having an acetaldehyde/ethanol weight ratio of from about 0.005 to about 0.05, an ethyl acetate/ethanol weight ratio of from about 0.0001 to about 0.005, and an ethyl butyrate/ethanol weight ratio of from about 0.0001 to about 0.005; then
   (b) passing the essence through a solid adsorbent to produce a first effluent, where the passage is stopped at a time between:
      (i) about the time when ethyl acetate reaches its maximum concentration (ppm by weight) in the effluent; and
      (ii) about the time when the concentration (ppm by weight) of ethyl butyrate in the effluent again becomes equal to its concentration in the original essence, after the time when the concentration of ethyl butyrate in the effluent reaches its maximum concentration; then (c) recycling at least about 10% by weight of the first effluent through the adsorbent to recover a second effluent, where the recycling is stopped when the first effluent is exhausted.

4. A process for making an improved citrus aqueous essence comprising the steps of:
  (a) obtaining a citrus aqueous essence having an acetaldehyde/ethanol weight ratio of from about 0.005 to about 0.05, an ethyl acetate/ethanol weight ratio of from about 0.0001 to about 0.005, and an ethyl butyrate/ethanol weight ratio of from about 0.0001 to about 0.005; then
  (b) passing the essence through a solid adsorbent to produce a first effluent, where the passage is stopped at a time between:
    (i) about the time when ethyl acetate reaches its maximum concentration (ppm by weight) in the effluent; and
    (ii) about the time when the concentration (ppm by weight) of ethyl butyrate in the effluent again becomes equal to its concentration in the original essence, after the time when the concentration of ethyl butyrate in the effluent reaches its maximum concentration; then
  (c) recycling at least about 10% by weight of the first effluent through the adsorbent to recover a second effluent, where the recycling is stopped at a time between:
    (i) about the first occurrence of hexanal in the effluent; and
    (ii) about the time when the concentration (ppm by weight) of hexanal in the effluent again becomes equal to its concentration in the original essence, after the time when the concentration of hexanal in the effluent reaches its maximum concentration.

5. A process according to claim 3 or 4 wherein the essence of part (a) contains at least about 500 ppm by weight acetaldehyde, at least about 10 ppm by weight ethyl acetate, and at least about 10 ppm by weight ethyl butyrate.

6. A process according to claim 3 or 4 wherein the solid adsorbent is activated carbon.

7. An orange aqueous essence prepared according to the process of claim 3 or 4 wherein the acetaldehyde/ethanol weight ratio is from about 0.005 to about 0.05, the ethyl acetate/ethanol weight ratio is from about 0.0001 to about 0.005, the ethyl butyrate/ethanol weight ratio is from about 0.0001 to about 0.005, and the ethyl butyrate/hexanal weight ratio is at least about 5.

8. A process for making an improved citrus aqueous essence from a starting essence having an excess of ethyl vinyl ketone, comprising the steps of:
  (a) obtaining a citrus aqueous essence having an acetaldehyde/ethanol weight ratio of from about 0.005 to about 0.05, an ethyl acetate/ethanol weight ratio of from about 0.0001 to about 0.005, an ethyl butyrate/ethanol weight ratio of from about 0.0001 to about 0.005, and an ethyl vinyl ketone/ethanol weight ratio of at least about 0.00003; then
  (b) passing the essence through a solid adsorbent to produce a first effluent, where the passage is stopped at a time between:
    (i) about the time when ethyl acetate reaches its maximum concentration (ppm by weight) in the effluent; and
    (ii) about the time when the concentration (ppm by weight) of ethyl butyrate in the effluent again becomes equal to its concentration in the original essence, after the time when the concentration of ethyl butyrate in the effluent reaches its maximum concentration; then
  (c) recovering the first effluent and setting aside a portion of the effluent containing ethyl vinyl ketone so that at least about 75% by weight of the ethyl vinyl ketone of the starting essence is removed; then
  (d) recycling at least about 10% by weight of the remaining first effluent through the adsorbent to recover a second effluent, where the recycling is stopped when the first effluent is exhausted.

9. A process for making an improved citrus aqueous essence from a starting essence having an excess of ethyl vinyl ketone, comprising the steps of:
  (a) obtaining a citrus aqueous essence having an acetaldehyde/ethanol weight ratio of from about 0.005 to about 0.05, an ethyl acetate/ethanol weight ratio of from about 0.0001 to about 0.005, an ethyl butyrate/ethanol weight ratio of from about 0.0001 to about 0.005, and an ethyl vinyl ketone/ethanol weight ratio of at least about 0.00003; then
  (b) passing the essence through a solid adsorbent to produce a first effluent, where the passage is stopped at a time between:
    (i) about the time when ethyl acetate reaches its maximum concentration (ppm by weight) in the effluent; and
    (ii) about the time when the concentration (ppm by weight) of ethyl butyrate in the effluent again becomes equal to its concentration in the original essence, after the time when the concentration of ethyl butyrate in the effluent reaches its maximum concentration; then
  (c) recovering the first effluent and setting aside a portion of the effluent containing ethyl vinyl ketone so that at least about 75% by weight of the ethyl vinyl ketone of the starting essence is removed; then
  (d) recycling at least about 10% by weight of the remaining first effluent through the adsorbent to recover a second effluent, where the recycling is stopped at a time between:
    (i) about the first occurrence of hexanal in the effluent; and
    (ii) about the time when the concentration (ppm by weight) of hexanal in the effluent again becomes equal to its concentration in the original essence, after the time when the concentration of hexanal in the effluent reaches its maximum concentration.

10. A process according to claim 8 or 9 wherein in step (c) the effluent of step (b) is recovered as a number of fractions, and fractions containing ethyl vinyl ketone are set aside.

11. A process according to claim 8 or 9 wherein the essence of part (a) contains at least about 500 ppm by weight acetaldehyde, at least about 10 ppm by weight ethyl acetate, and at least about 10 ppm by weight ethyl butyrate.

12. A process according to claim 8 or 9 wherein the solid adsorbent is activated carbon.

13. An orange aqueous essence prepared according to the process of claim 8 or 9 wherein the acetaldehyde/ethanol weight ratio is from about 0.005 to about 0.05, the ethyl acetate/ethanol weight ratio is from about 0.0001 to about 0.005, the ethyl butyrate/ethanol weight ratio is from about 0.0001 to about 0.005, the ethyl butyrate/hexanal weight ratio is at least about 5, and the ethyl vinyl ketone/ethanol weight ratio is less than about 0.00002.

14. A process according to claim 8 or 9 wherein the ethyl vinyl ketone-containing fractions removed in step (c) are further processed by passing them through a solid adsorbent and then recovering the effluent.

* * * * *